United States Patent [19]
Chuang

[11] Patent Number: 6,037,499
[45] Date of Patent: Mar. 14, 2000

[54] AROMATIC DIAMINES AND POLYIMIDES BASED ON 4,4'-BIS-(4-AMINOPHENOXY)-2,2' OR 2,2',6,6'-SUBSTITUTED BIPHENYL

[75] Inventor: Chun-Hua K. Chuang, Brecksville, Ohio

[73] Assignee: The United States of America as represented by the Administrator of the National Aeronautics and Space Administration, Washington, D.C.

[21] Appl. No.: 09/226,633

[22] Filed: Dec. 24, 1998

Related U.S. Application Data

[62] Division of application No. 09/012,173, Jan. 23, 1998, Pat. No. 5,939,521.

[51] Int. Cl.$^7$ .................................................. C07C 217/90
[52] U.S. Cl. .......................... 564/430; 528/125; 528/128; 528/170; 528/172; 528/173; 528/174; 528/175; 528/179; 528/183; 528/185; 528/188; 528/220; 528/229; 528/350; 528/353
[58] Field of Search ............................. 564/430; 528/125, 528/128, 170, 172, 173, 174, 175, 179, 183, 185, 188, 220, 229, 350, 353

[56] References Cited

U.S. PATENT DOCUMENTS

| | | | |
|---|---|---|---|
| 3,745,149 | 7/1973 | Serafini et al. | 260/65 |
| 5,091,505 | 2/1992 | Serafini et al. | 528/353 |
| 5,322,924 | 6/1994 | Chuang et al. | 528/353 |
| 5,844,065 | 12/1998 | Liaw et al. | 528/353 |

*Primary Examiner*—Peter O'Sullivan
*Attorney, Agent, or Firm*—Kent N. Stone

[57] ABSTRACT

This invention relates the novel diamines, the polyimide oligomers and the polyimides derived therefrom and to the method of preparing the diamines, oligomers and the polyimides. The thermoplastic polyimides derived from the aromatic diamines of this invention are characterized as having a high glass transition temperature, good mechanical properties and improved processability in the manufacture of adhesives, electronic and composite materials for use in the automotive and aerospace industry. The distinction of the novel aromatic diamines of this invention is the 2,2',6,6'-substituted biphenyl radicals which exhibit noncoplanar conformation that enhances the solubility of the diamine as well as the processability of the polyimides, while retaining a realatively high glass transition temperature and improved mechanical properties at useful temperature ranges.

11 Claims, No Drawings

AROMATIC DIAMINES AND POLYIMIDES BASED ON 4,4'-BIS-(4-AMINOPHENOXY)-2,2' OR 2,2',6,6'-SUBSTITUTED BIPHENYL

PRIOR U.S. APPLICATION

This Application is a Division of application Ser. No. 09/012,173 filed Jan. 23, 1998 now U.S. Pat. No. 5,939,521.

ORIGIN OF THE INVENTION

The invention described herein was made by an employee of the United States Government and may be manufactured and used by or for the Government for governmental purposes without payment of any royalties thereon or therefore.

BACKGROUND OF THE INVENTION

FIELD OF THE INVENTION

This invention relates to novel aromatic diamines, the polyimide oligomers and the polyimides derived from said diamines and polyimide oligomers. More specifically, this invention relates the novel diamines, the oligomers and the polyimides derived therefrom and to the method of preparing the diamines, polyimide oligomers and the polyimides. The polyimides derived from the aromatic diamines of this invention are characterized as having high glass transition temperatures, good mechanical properties and improved processability in the manufacture of adhesives, electronics and composite materials. The distinction of the novel aromatic diamines of this invention over the prior art resides in the 2,2'- and 2,2', 6,6'-substituted biphenyl moieties which exhibit noncoplanar conformation that enhances the solubility of the diamine as well as the processability of the polyimides, while retaining a relatively high glass transition temperature and improved mechanical properties at useful temperature ranges.

The novel aromatic diamines and the polyimides derived therefrom in accordance with this invention can be characterized by the following formula and by the disclosure more specifically set forth herein.

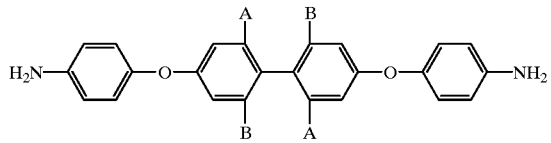

BACKGROUND OF DISCLOSURE

Polymeric materials having improved high-temperature characteristics have been required to enhance the performance and to reduce the weight of various industrial materials in the fields of electronic devices, aeronautical equipment and machinery. The polyimides are known to have the required mechanical strength, dimensional stability, flame retardance, low coefficient of thermal expansion, and electrical insulation properties in addition to excellent high-temperature resistance. Polyimides of high molecular weight, however, generally have a high softening point and are insoluble in most organic solvents. Therefore, many difficulties have been encountered in the use of polyimides.

While there are a number of prior art thermoplastic polyimides that have improved heat resistance and mechanical strength compared to the general purpose plastics, there is still a need for thermoplastic polyimide resins having improved heat-resistance, and good mechanical characteristics.

For example, polyimides have been prepared from the following 4,4'-bis(4-aminophenoxy)-biphenyl,

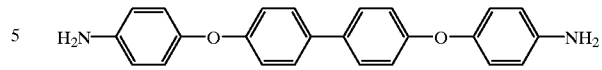

This particular diamine is insoluble in many of the common solvents such as ethanol, acetone or N,N-dimethylformamide (DMF), but is soluble only in N-methyl-2-pyrrolidinone (NMP).

Further, in the prior art, for example, U.S. Pat. No. 5,344,986, Oren et.al. discloses a composition and the process of making a 4,4'-bis(4-amino-substituted phenoxy) diamine. U.S. Pat. No. 5,268,487 Yang et.al discloses the use of 4,4'-bis(4-aminophenoxy) 3,3'-dimethyl-biphenyl and 4,4'-bis(4-aminophenoxy)-3,3',5,5'-tetramethyl-biphenyl for the preparation of polyimides. Although U.S. Pat. Nos. 5,344,986 and 5,268,487 disclose structures similar to the diamines of this invention, the 2,2'- or 2,2',6,6'-substituents in the diamine of this invention improve the glass transition temperature of the corresponding polyimides and enhanced the solubility of the diamine monomer. Recently, polyimides containing 2,2'-substituted benzidine was found to possess excellent thermo-oxidative stability as well as enhanced processability as described in U.S. Pat. Nos. 5,071,997; 5,487,918; and 5,322,924.

However, the glass transition temperature of the thermoset polyimide (IV) derived from 2,2'-bis[-4-(4-aminophenoxy)phenyl] propane (BAPP) exhibits a lower glass transition temperature (~280° C.) than the polyimides derived from the diamine of this invention [$T_g$=307° C.]. Moreover, the thermoset polyimides derived from the diamines of this invention exhibited physical properties 30% higher than the properties of the polyimides derived from 2,2-bis[4-(4-aminophenoxy)phenyl] propane. The advantage of the diamine of this invention is the fact that the 2,2'- or 2,2',6,6'-substituted biphenyl moieties exhibit noncoplanar conformation, which enhances the solubility of the diamine as well as the processability of the polyimides, while retaining a relatively high glass transition temperature and better mechanical properties at a useful temperature range. In addition, the monomeric diamines of this invention are soluble in most of the common organic solvent such as acetone, tetrahydrofuran, etc. The substituents in the diamine improves the solubility of the diamine in solvents in comparison to the unsubstituted diamines of the prior art.

SUMMARY OF THE INVENTION

This invention relates to novel substituted aromatic diamines, the polyimide oligomers and polyimide resins derived from said aromatic diamines. The polyimides are characterized as having high glass transition temperatures ($T_g$), good mechanical strength and are easy to process in the manufacture of electronics, adhesives and composites for use in the automotive, space, aeronautical and building industries.

More specifically, this invention relates to aromatic diamines characterized by Formula I:

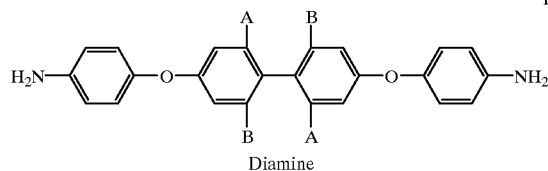

Diamine and the use of said diamines in the preparation of lower molecular weight polyimide oligomers (Formula III) and high molecular weight thermoplastic polyimides (Formula II) characterized by the following formulae:

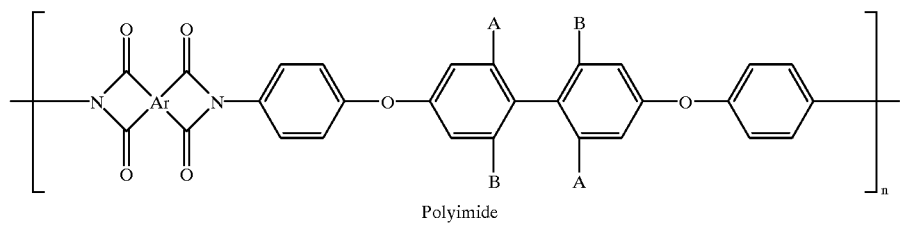

Polyimide

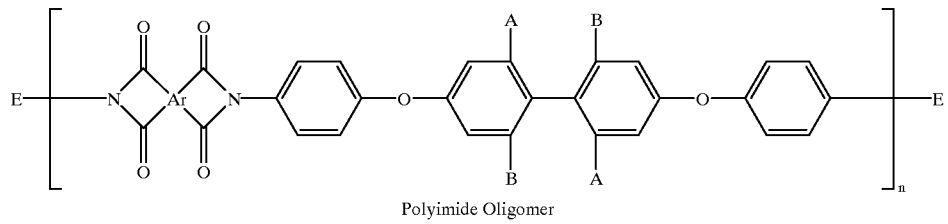

Polyimide Oligomer

In formulae I, II and III, A is a radical selected from the Group consisting of an alkyl radical of 1 to 4 carbons, —$CF_3$, aryl, halogen, —OR where R is an alkyl, aryl or substituted aryl radical of 1 to 8 carbons, and —$OCX_3$ where X is halogen, and B is a radical selected from the Group consisting of hydrogen, an alkyl radical of 1 to 4 carbons, —$CF_3$, aryl, halogen, —OR where R is an alkyl, aryl, or substituted aryl radical of 1 to 8 carbons, and —$OCX_3$ where X is halogen. In formulae II and III, Ar is a tetravalent aromatic group such as a dianhydride. In formulae II and III, "n" is a whole number ranging from 2 to 100 and in formula III, E is an unreactive aromatic chain blocker such as aniline, phthalic anhydride and the like or a reactive unit which can undergo further crosslinking to form a network.

Accordingly, an object of this invention is to provide an aromatic diamine for use in the preparation of thermoplastic polyimides characterized as having high glass transition temperatures and good mechanical strengths for the preparation of various industrial products.

It is another object of this invention to provide aromatic diamines and polyimides that are easy to process due to the improved solubility of these products in various organic solvents for the manufacture of electronics, adhesives, and particularly the manufacture of composites useful in the space and aeronautical industries.

It is a further object of this invention to provide the method of preparing high molecular weight polyimides from the novel substituted aromatic diamines.

It is still a further object of this invention to provide high molecular weight polyimides useful in the preparation of polyimide resin composites having improved mechanical properties.

These and other objects of the invention will become apparent from a further and more detailed description of the invention.

DETAILED DESCRIPTION OF THE INVENTION

This invention relates to novel substituted aromatic diamines and the use of these diamines in the preparation of polyimide oligomers and high molecular weight thermoplastic polyimides. The distinction of the diamine of this invention over the prior art is due to the 2,2'-or 2,2',6,6'-substituted biphenyl radicals in the diamine which exhibit noncoplanar conformation, that enhances the solubility of the diamine as well as the processability of the polyimides derived therefrom, while retaining relatively high glass transition temperatures and better mechanical properties.

An example of preparing the substituted aromatic diamines of this invention is the following:

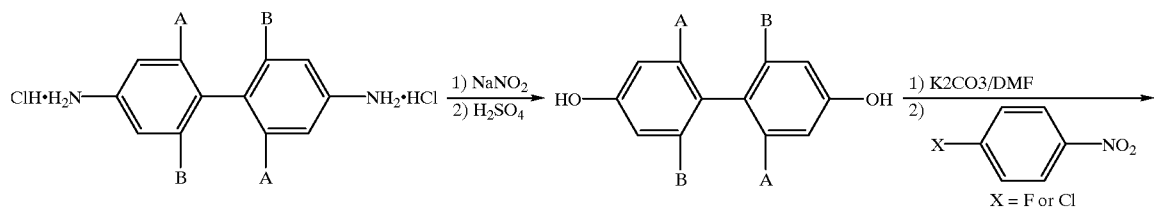

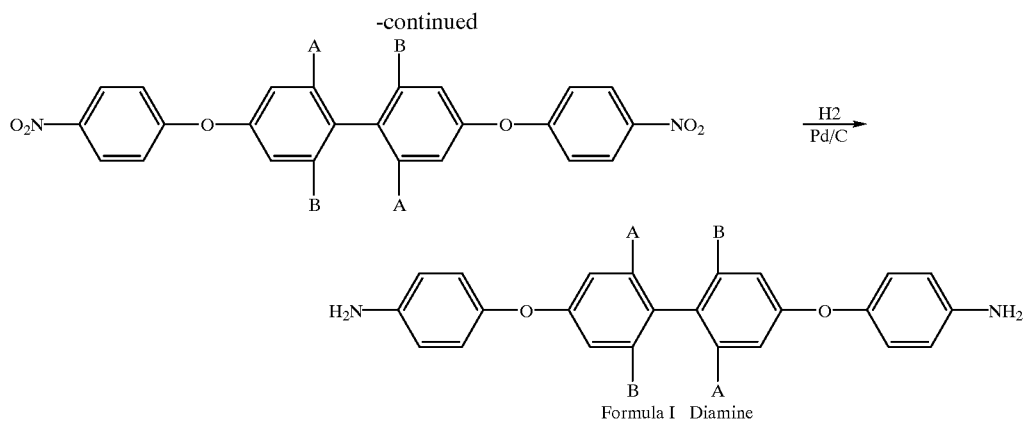

Formula I Diamine

More specifically, the synthesis of 4,4'-bis(4-aminophenoxy)-2,-2'-dimethylbiphenyl is as follows:

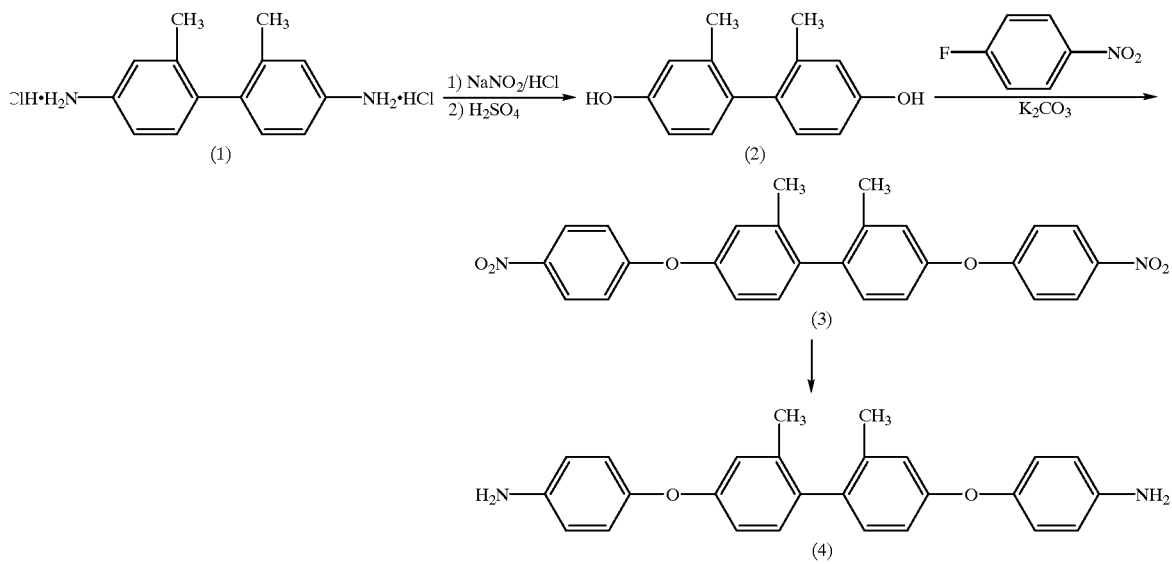

EXAMPLE I

Synthesis of 2,2'-dimethyl-4,4'-biphenol (2)

To a 1000 ml of flask, 2,2'-dimethylbenzidine dihydrochloride (53.4 g, 10.15 mol) (1) was added as wet cakes, containing 26% moisture, as received along with 200 ml. of distilled water and 30 ml. of concentrated HCl. The resulting heterogeneous reaction mixture was stirred at 0° C. Then a solution of sodium nitrite (22.77 g, 0.33 mol) in 40 ml. of water was added dropwise to the above solution over the period of 1 hour at 0° C. under nitrogen to form diazonium salts. Separately, a two phase solution containing 75 ml. of sulfuric acid in 250 ml. of water and 125 ml of 1,2 dichloroethane in a 2000 ml. round-bottom flask was stirred vigorously into a one phase system at 85–90° C. Then the diazonium solution was added dropwise to the above two phase solution with very efficient stirring for 1–2 hours until no more nitrogen was evolved due to the decomposition of diazonium slats. During the process, the diazonium salts were decomposed by aqueous sulfuric acid to form the biphenol and were immediately extracted to the organic layer. The reaction mixture was cooled down, and the organic layer was separated and dried over magnium sulfate. The solvent was concentrated to half of its original volume and then cooled in the refrigerator overnight to induce crystallization. The resulting solids were collected and washed with 1,2-dichloroethane/hexane=15/85 to remove the dark color impurities to afford 19.66 g (62%) as the first crop. mp=106–108° C.

Synthesis of 4,4'-bis(4-nitrophenoxy)-2,2'-dimethylbiphenyl (3)

2,2'-Dimethylbiphenol (2) (42.8 g, 0.2 mol) was dissolved in 250 ml of N,N-dimethylformaide (DMF), and then potassium carbonate (60.8 g, 0.44 mol) and 4-fluoro-nitrobenzene (59.22 g, 0.42 mol) were added. The reaction mixture was heated to reflux for 20 hours overnight. The reaction mixture was filtered to remove potassium carbonate, then the solution was concentrated to ⅓ of its original volume in a rotary evaporator. Subsequently, water was added to the DMF solution to precipitate out the product in quantitative yield, and then the product was washed with ethanol to remove trace of unreacted 4-fluoro-nitrobenzene. The crude product (mp 146–147° C.) is pure enough for next step.

Synthesis of 4,4'-bis(4-aminophenoxy)-2,2'-dimethylbiphenyl (4)

4,4'-Bis(4-nitrophenoxy)-2,2'-dimethylbiphenyl (80 g) was dissolved in 350 ml of DMF and added carefully to a hydrogenation bottle containing 8 gm of 5% Pt/C. The solution was subjected to hydrogenation at 100° C. for 3 hours. Then 100 ml of water and 3 g of decolorizing charcoal were added and heated for 5 min. The solution was then filtered through a Celite pad and 1000 ml of water was added. The reaction mixture became a mixture of fluffy solid and a sticky resin and was stirred for 1 hour to give a tan colored solid. The solid was removed by filtration, crushed with a mortar and pestel and then stirred with 1000 ml of water for 1 hour. The solid was collected by filtration and dried to afford 59.2 g (85%) of the product mp=140° C.

The following is an example of preparing a polyimide of this invention.

EXAMPLE II 4,4'-Bis(4-aminophenoxy)-2,2'-dimethylbiphenyl (0.99 g, 2.5 mmol) and 3,3',4,4'-benzophenonetetracarboxylic dianhydride (0.8 g, 2.5 mmol) were mixed with 10 g of dry N-methyl-2-pyrrolidinone(NMP), and the reaction was stirred at room temperature overnight under nitrogen to obtain very viscous poly(amic acid) solution. The viscous solution was heated to reflux at 200° C. for 2–3 hours. The resulting polyimide solution was diluted with additional dry NMP to the consistency of a maple syrup, and then precipitated into ethanol to obtain colorless fibers.

More specifically, the aromatic diamines of formula I can be polymerized with effective amounts of at least one aromatic tetracarboxylic acid, the anhydrides or the esters of said tetracarboxylic acid to obtain the corresponding polyimides. The process of preparing the thermoplastic, high molecular weight polyimides (n=2 to 100) of this invention is described by the reaction of a dianhydride and the aromatic diamine of formula (I) as follows:

The Ar group indicates an aliphatic or aromatic radical having a valence of four.

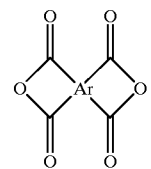

An alternative embodiment of this invention includes the preparation of polyimide copolymers containing the aromatic diamine of formula I. For example, a mixture of two or more different dianhydrides or two different diamines can be used where at least one of them is the diamine of formula I. Specific examples of the preferred anydrides which may be employed in this invention includes pyromellitic dianhydride, 4,4'-(hexafluoroisopropylidene)-bis(phthalic anhydride), 3,3',4,4'-benzophenonetetracarboxylic dianhydride, 2,3,3',4'-benzophenonetetracarboxylic dianhydride, 3,3',4,4'-biphenyltetracarboxylic dianhydride, 2,3,3',4'-biphenyltetracarboxylic dianhydride, bis(3,4-dicarboxyphenyl)ether dianhydride, bis(3,4-dicarboxyl) sulfone dianhydride, 4,4'-(p-phenylenedioxy)diphthalic anhydride, 1,2,5,6-naphthlenetetracarboxylic dianhydride, 2,3,6,7-naphthlenetetracarboxylic dianhydride, 1,4,5,8-naphthalenetetracarboxylic dianhydride etc. and the corresponding tetracarboxylic acids or esters.

In addition, the polyimide oligomers of this invention can be prepared with an aromatic dianhydride, its diester or diacid reacted with the diamine of formula I and a chain stopping reactant capable of further crosslinking. These reactants can be mixed in the ratios needed to obtain the polyimide oligomers of formula III. The oligomers can undergo further crosslinking through the reactive units associated with endcap E as follows:

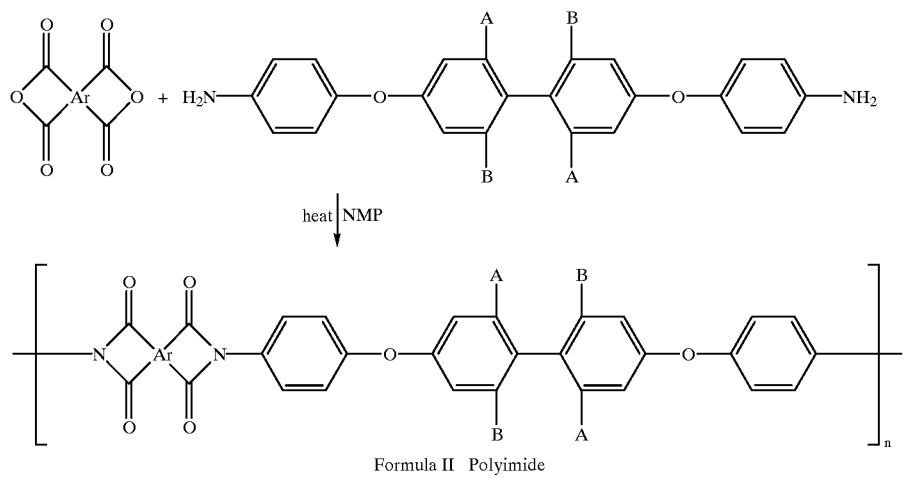

Formula II Polyimide

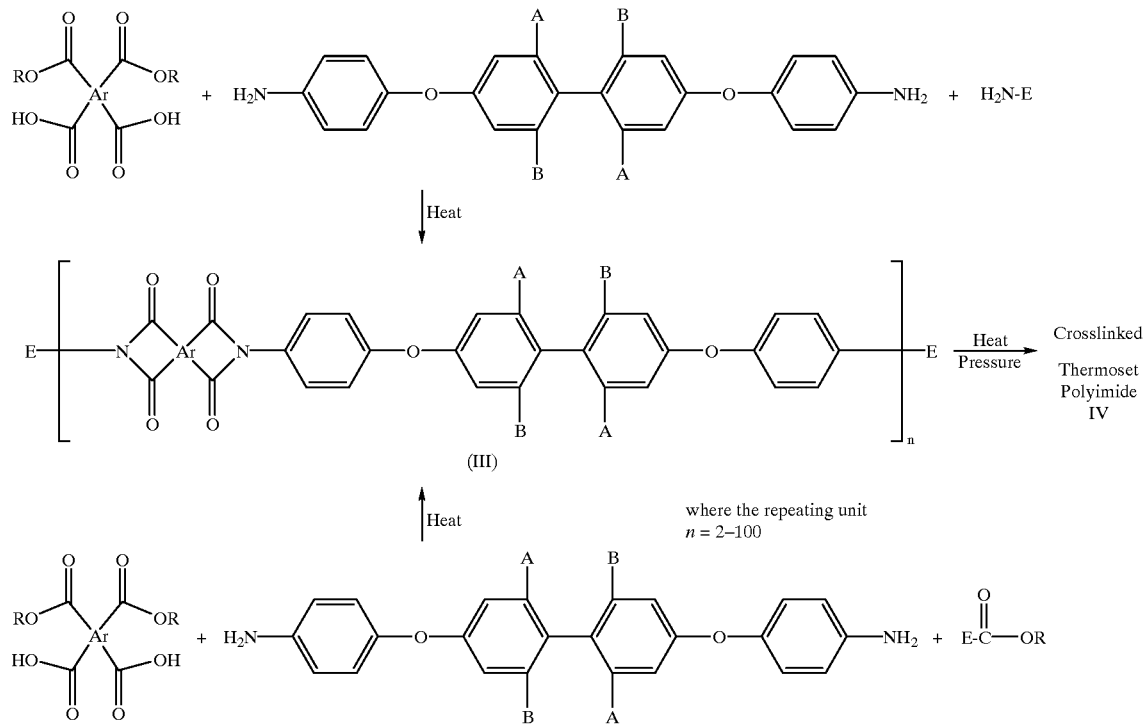

In the above reaction, E can be an unreactive chain blocker such as aniline or a phthalic ester or phthalic anhydride. E can also be a reactive unit wherein E further crosslinks with linear oligomeric chains to form a network IV. Specific examples of some preferred reactive units or reactive endcaps (E) are as follows:

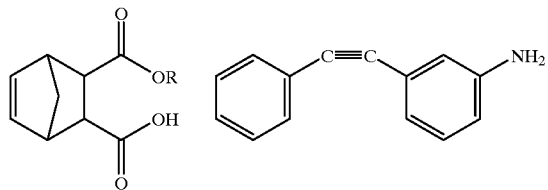

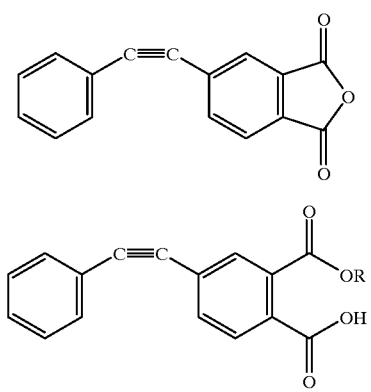

-continued

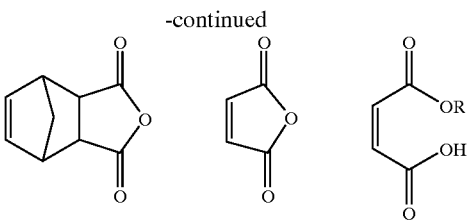

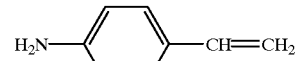

The use of the aromatic diamine of formula I improves the processability of the resulting polyimides while retaining a relative high Tg, and thereby raises the useful temperature range. Furthermore, higher $T_g$ generally translated into better mechanical properties over useful temperature ranges.

Specific examples of the preferred aromatic diamines of this invention for purposes of preparing the thermoplastic polyimides of this invention include:

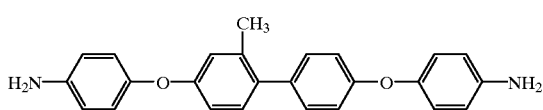

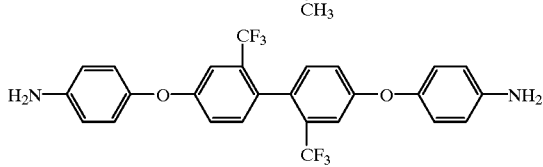

-continued

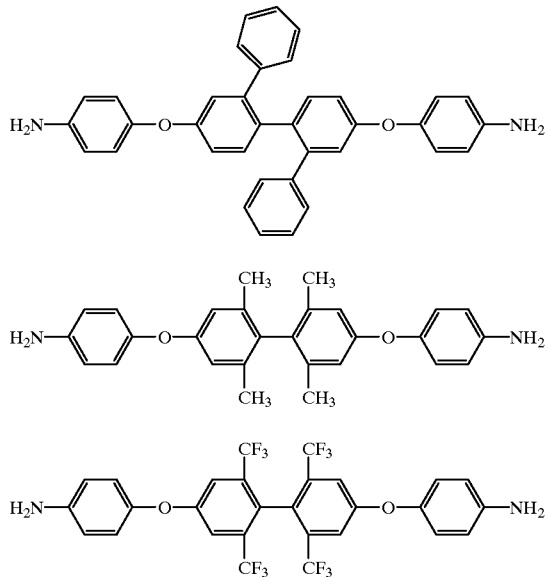

One of the objects of this invention was to evaluate several resins for 500–550° F. applications, see Table I, using a solvent assisted resin transfer molding (RTM) process. PMR-15, APDB-20 and AMB-21 polyimide composites were prepared from 3,3',4,4'-benzophenone tetracarboxylic acid, dimethyl ester (BTDE) and each respective diamine; namely, 4,4'-methylene dianiline (MDA), 4,4'-bis(4-aminophenoxy)-2,2'-dimethylbiphenyl (APDB) and 2,2'-bis[4-(4-aminophenoxy)phenyl]propane (BAPP), using Nadic acid ester (NE) as the endcap. Alternately, BAPA-16 composites were prepared from bisphenol-A tetracarboxylic acid, dimethyl ester, p-phenylenediamine (p-PDA) and nadic ester (NE). The glass transition temperature ($T_g$), the thermo-oxidative stability and the mechanical properties of these polyimide/carbon fiber (T650-35) composites were compared to PMR-15; see the data in Table II.

Monomer solutions of the polyimides (Table I) were prepared from 50 wt % methanol or methanol-acetone. The prepreg tapes were made by brush application of monomer solution onto drum-wound T650-35 carbon fibers, and subsequently dried. The laminates were then fabricated from 12 plies of unidirectional prepreg by a simulated autoclave preocess. The $T_g$ of these polyimide composites were measured by dynamic mechanical analysis (DMA) on a Rheometrics RMS 800 and thermal mechanical analysis (TMA).

The DMA and TMA data (Table II) shows that APDB-20 composites display higher $T_g$ than either AMB-21 or BAPA-16, because the 2,2'-dimethylbiphenyl moiety is more rigid than the isopropylidene [—$C(CH_3)_2$—] group present in AMB-21 and BAPA-16. Furthermore, the two methyl substituents on APDB-20 forces the biphenyl rings into adopting a noncoplanr conformation, which enhances the solubility of the APDB-20 diamine and the processability of the APDB-20 oligomers. Essentially, APDB-20 polyimide can be processed like AMB-21. The mechanical properties of PMR-15, APDB-20 and AMB-21 composites at 550° F. follow the trend of higher $T_g$'s leading to better mechanical properties in the order of PMR-15>APDB-20>AMB-21. The isothermal aging study at 500° F.(288° C.) indicated that APDB-20 exhibited higher weight loss, but still retained about 70% of mechanical properties compared to PMR-15. This phenomenon is attributed to the loss of methyl substituents on APDB-20 due to thermo-oxidative degradation, however, the polymer backbone apparently still remains intact. When testing at 500° F.(260° C.), APDB-20, AMB-21 and BAPA-16 all displayed comparable initial mechanical properties, except the flexural strength is slightly lower in BAPA-16.

TABLE I
| Molar Ratio | Endcap 2 | Dimethyl Esters n | Diamine n + 1 | Repeating unit (n) |
|---|---|---|---|---|
| APDB-20 | 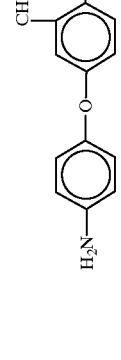 NE |  BTDE | 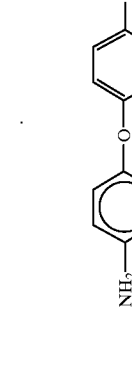 APDB | 2 |
| AMB-21 | NE | BTDE | 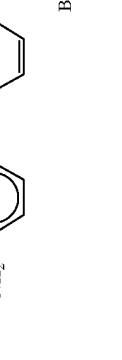 BAPP | 2.087 |
| PMR-15 | NE | BTDE | 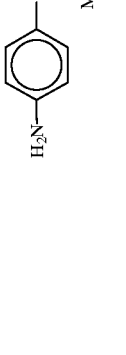 MDA | |
| BAPA-16 | NE | 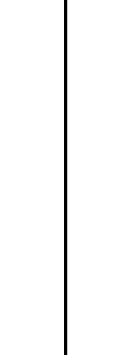 Bisphenol A DE |  PDA | |

TABLE II

Tg's of Polyimide Composites by DMA[a] and TMA[b]

| Property | G' (onset)[c] °C. | | Tan δ °C. | | TMA °C. | |
|---|---|---|---|---|---|---|
| Resin | NPC[d] | APC[e] | NPC | APC | NPC | APC |
| APDB-20 | 282 | 307 | 320 | 334 | 269 | 307 |
| AMB-21 | 241 | 280 | 270 | 304 | 243 | 278 |
| BAPA-16 | 277 | 281 | 306 | 308 | 252 | 273 |
| PMR-15 | 345 | 348 | 375 | 376 | 320 | 348 |

[a]DMA = Dynamical mechanical analysis at a heating rate of 5° C./min by a Rheometric RMS 800, using a torsional rectangular geometry at 1 Hz and 0.05% tension.
[b]TMA = Thermal mechanical analysis by expansion probe, with 5 g load and a heating rate of 10° C./min.
[c]G' = Onset decline of strorage modulus
[d]NPC = No postcure
[e]APC = Air postcure at 600° F. (315° C.) for 16 h.

In comparison, the APDB-20 polyimide, which contains 2,2'-dimethyl biphenyl moiety, exhibited higher $T_g$ and mechanical properties than AMB-21 or BAPA-16, that consisted of the flexible isopropylidene group. Although the ether linkages in these polyimides tend to improve the processability, they generally result in lower $T_g$ and poorer thermo-oxidative stability, in comparison to PMR-15.

The polyimide and carbon fiber composites of this invention can be used as a lightweight replacement for metallic components in the aerospace field, due to their outstanding thermo-oxidative stability and mechanical properties. The polyimide matrices offer better property retention over epoxies or bismaleimides in high temperature environment. The polyimide composites are often fabricated using hand lay-up laminates by vacuum bag autoclave or compression molding methods, instead of injection or resin transfer molding (RTM). Carbon fibers which can be used with polyimide include acrylic carbon fiber, rayon-based carbon fiber, lignin-based carbon fiber and pitch-based carbon fiber. The form of carbon fiber can be chopped strand, roving and woven fabric. In order to apply the polyimide to the carbon fiber, the diamine monomer is dissolved in a solvent such as methanol, acetone, N,N-dimethylacetamide, or N-methyl-2-pyrrolidione. The amount of carbon fiber and polyimide resin are mixed to make the composition of this invention ranges from 10 to 70 parts by weight of the carbon fiber to from 90 to 30 parts by weight of the polyimide resin.

Additives that can be incorporated with the polyimide composition of this invention includes talc, calcium carbonate, mica, and other fillers, glass fiber, ceramic fiber and other fibrous reinforcements. These additives can be used in amounts depending on the quality and performance of the composition. The polyimide resin composition can be processed into desired articles by injection molding, extrusion forming, transfer molding, compression molding and other known processing methods. The polyimide resin compositions of this invention have excellent mechanical strength at high temperatures and therefore can be used for mechanical parts which requires high mechanical strength at high temperatures.

While this invention has been described by a number of specific examples, it is obvious that there are other variations and modifications which can be made without departing from the spirit and scope of the invention as particularly set forth in the appended claims.

The invention claimed:

1. An aromatic diamine characterized by the formula:

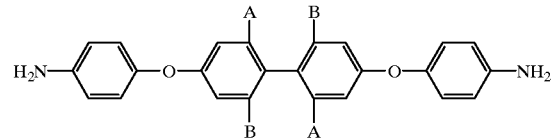

wherein A is a radical selected from the Group consisting of —$CF_3$, aryl, halogen, —OR where R is an alkyl, aryl or substituted aryl radical of 1 to 8 carbons, and —$OCX_3$ where X is halogen, and B is a radical selected from the Group consisting of hydrogen, an alkyl group of 1 to 4 carbons, —$CF_3$, aryl, halogen, —OR where R is an alkyl, aryl, or substituted aryl radical of 1 to 8 carbons, and —$OCX_3$ where X is halogen.

2. The aromatic diamine of claim 1 wherein B is hydrogen.

3. The aromatic diamine of claim 1 wherein B is an alkyl radical of 1 to 4 carbons.

4. The aromatic diamine of claim 1 wherein A is a $CF_3$ group.

5. The aromatic diamine of claim 1 wherein A is an aryl radical and B is hydrogen.

6. The aromatic diamine of claim 1 wherein A is $CF_3$ and B is $CF_3$.

7. The aromatic diamine of claim 2 wherein A is an aryl radical and B is hydrogen.

8. The aromatic diamine of claim 1 wherein A and B are aryl radicals.

9. The aromatic diamine of claim 1 wherein A is an —OR radical where R is an alkyl group and B is an —OR radical where R is an aryl group.

10. The aromatic diamine of claim 1 wherein A is an —$OCX_3$ radical where X is halogen and B is an —$OCX_3$ radical where X is halogen.

11. The aromatic diamine of claim 10 wherein X is chlorine.

* * * * *